United States Patent
Fujimura

(10) Patent No.: US 9,919,343 B2
(45) Date of Patent: Mar. 20, 2018

(54) ULTRASOUND TRANSDUCER AND ULTRASOUND ENDOSCOPE

(71) Applicant: OLYMPUS CORPORATION, Tokyo (JP)

(72) Inventor: Takanao Fujimura, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/422,527

(22) Filed: Feb. 2, 2017

(65) Prior Publication Data

US 2017/0144194 A1 May 25, 2017

Related U.S. Application Data

(63) Continuation of application No. PCT/JP2015/079185, filed on Oct. 15, 2015.

(30) Foreign Application Priority Data

Nov. 21, 2014 (JP) .................................. 2014-236901

(51) Int. Cl.
 *H01L 41/08* (2006.01)
 *B06B 1/06* (2006.01)

(52) U.S. Cl.
 CPC ........ *B06B 1/0622* (2013.01); *B06B 2201/20* (2013.01); *B06B 2201/55* (2013.01); *B06B 2201/76* (2013.01)

(58) Field of Classification Search
 CPC .............. B06B 1/0622; B06B 2201/20; B06B 2201/55; B06B 2201/76
 See application file for complete search history.

(56) References Cited

U.S. PATENT DOCUMENTS

| 4,440,025 A | * | 4/1984 | Hayakawa | ............ B06B 1/0633 310/334 |
| 4,462,092 A | * | 7/1984 | Kawabuchi | ........... B06B 1/0622 310/336 |

(Continued)

FOREIGN PATENT DOCUMENTS

| JP | 01146499 A | * | 6/1989 |
| JP | H01-146499 A | | 6/1989 |

(Continued)

OTHER PUBLICATIONS

International Search Report dated Dec. 28, 2015 issued in PCT/JP2015/079185.

(Continued)

*Primary Examiner* — J. San Martin
(74) *Attorney, Agent, or Firm* — Scully, Scott, Murphy & Presser, P.C.

(57) ABSTRACT

An ultrasound transducer includes: an acoustic matching layer bending with a predetermined curvature; a plurality of piezoelectric elements disposed on an inner face on a side of a curvature center of the acoustic matching layer in such a manner that the plurality of piezoelectric elements bend; a plurality of wirings including respective one ends electrically connected to the plurality of piezoelectric elements, respectively; a substrate to which respective other ends of the plurality of wirings are electrically connected; and a holding member provided on the plurality of wirings at a position partway of the plurality of wirings between the plurality of piezoelectric elements and the substrate, the holding member being configured to hold a pitch of the plurality of wirings so as to be a pitch that is equal to or smaller than a predetermined arrangement pitch of the plurality of piezoelectric elements.

12 Claims, 18 Drawing Sheets

(56) References Cited

U.S. PATENT DOCUMENTS

| | | | |
|---|---|---|---|
| 8,900,152 B2 * | 12/2014 | Ogawa | A61B 8/12 |
| | | | 600/101 |
| 2011/0248603 A1 * | 10/2011 | Tezuka | A61B 8/4405 |
| | | | 310/314 |
| 2017/0303893 A1 * | 10/2017 | Sato | A61B 8/4272 |

FOREIGN PATENT DOCUMENTS

| | | | |
|---|---|---|---|
| JP | 03054997 A * | 3/1991 | |
| JP | H06-041708 U | 6/1994 | |
| JP | 08079895 A * | 3/1996 | |
| JP | H08-172695 A | 7/1996 | |
| JP | 2001-198126 A | 7/2001 | |

OTHER PUBLICATIONS

Japanese Office Action dated Jul. 5, 2016 issued in JP 2016-528039.

* cited by examiner

W2≦W1

US 9,919,343 B2

ULTRASOUND TRANSDUCER AND ULTRASOUND ENDOSCOPE

CROSS REFERENCE TO RELATED APPLICATION

This application is a continuation application of PCT/JP2015/079185 filed on Oct. 15, 2015 and claims benefit of Japanese Application No. 2014-236901 filed in Japan on Nov. 21, 2014, the entire contents of which are incorporated herein by this reference.

BACKGROUND OF THE INVENTION

1. Field of the Invention

The present invention relates to an ultrasound transducer including a plurality of wirings electrically connecting a plurality of piezoelectric elements and a substrate, and an ultrasound endoscope.

2. Description of the Related Art

In an ultrasound endoscope that enables observation of an ultrasound image, which is a two-dimensional visible image of an area to be examined, an ultrasound transducer provided on the distal end side in an insertion direction of an insertion portion typically includes a plurality of divisional piezoelectric elements provided with respective GND electrodes and signal electrodes, and has a function that upon a voltage being externally applied to the respective GND and signal electrodes, radiates ultrasound to an area to be examined, along with vibration of the respective piezoelectric elements, and receives reflected sound from the area to be examined and converts the reflected sound into electric signals.

Also, transmission/reception of power and electric signals to/from the ultrasound transducer to/from the outside are performed by electrical connection of the an ultrasound signal transmission cable inserted inside the ultrasound endoscope to the signal electrodes of the respective piezoelectric elements.

Here, for the electrical connection of the ultrasound signal transmission cable to the respective piezoelectric elements, a configuration in which such electrical connection is made via a substrate is publicly known.

More specifically, a configuration in which respective signal wires of an ultrasound signal transmission cable are electrically connected to a plurality of pads provided on a substrate and signal electrodes of respective piezoelectric elements and the respective pads on the substrate are electrically connected via a plurality of wirings, and the ultrasound signal transmission cable is thereby electrically connected to the respective piezoelectric elements is known.

As described above, a configuration in which a substrate and a plurality of piezoelectric elements are electrically connected via a plurality of wirings is disclosed in, for example, Japanese Patent Application Laid-Open Publication No. 8-172695.

In recent years, for ultrasound image quality enhancement, a configuration of an ultrasound transducer in which resolution is enhanced by an increase in number divisional piezoelectric elements is publicly known.

SUMMARY OF THE INVENTION

An ultrasound transducer according to an aspect of the present invention includes: an acoustic matching layer bending with a predetermined curvature; a plurality of piezoelectric elements disposed on an inner face on a side of a curvature center of the acoustic matching layer in such a manner that the plurality of piezoelectric elements bend; a plurality of wirings including respective one ends electrically connected to the plurality of piezoelectric elements, respectively; a substrate to which respective other ends of the plurality of wirings are electrically connected; and a holding member provided on the plurality of wirings at a position partway of the plurality of wirings between the plurality of piezoelectric elements and the substrate, the holding member being configured to hold a pitch of the plurality of wirings so as to be a pitch that is equal to or smaller than the predetermined arrangement pitch of the plurality of piezoelectric elements.

Also, an ultrasound endoscope according to an aspect of the present invention includes the ultrasound transducer according to claim 1.

DETAILED DESCRIPTION OF THE PREFERRED EMBODIMENT(S)

Figure 1:
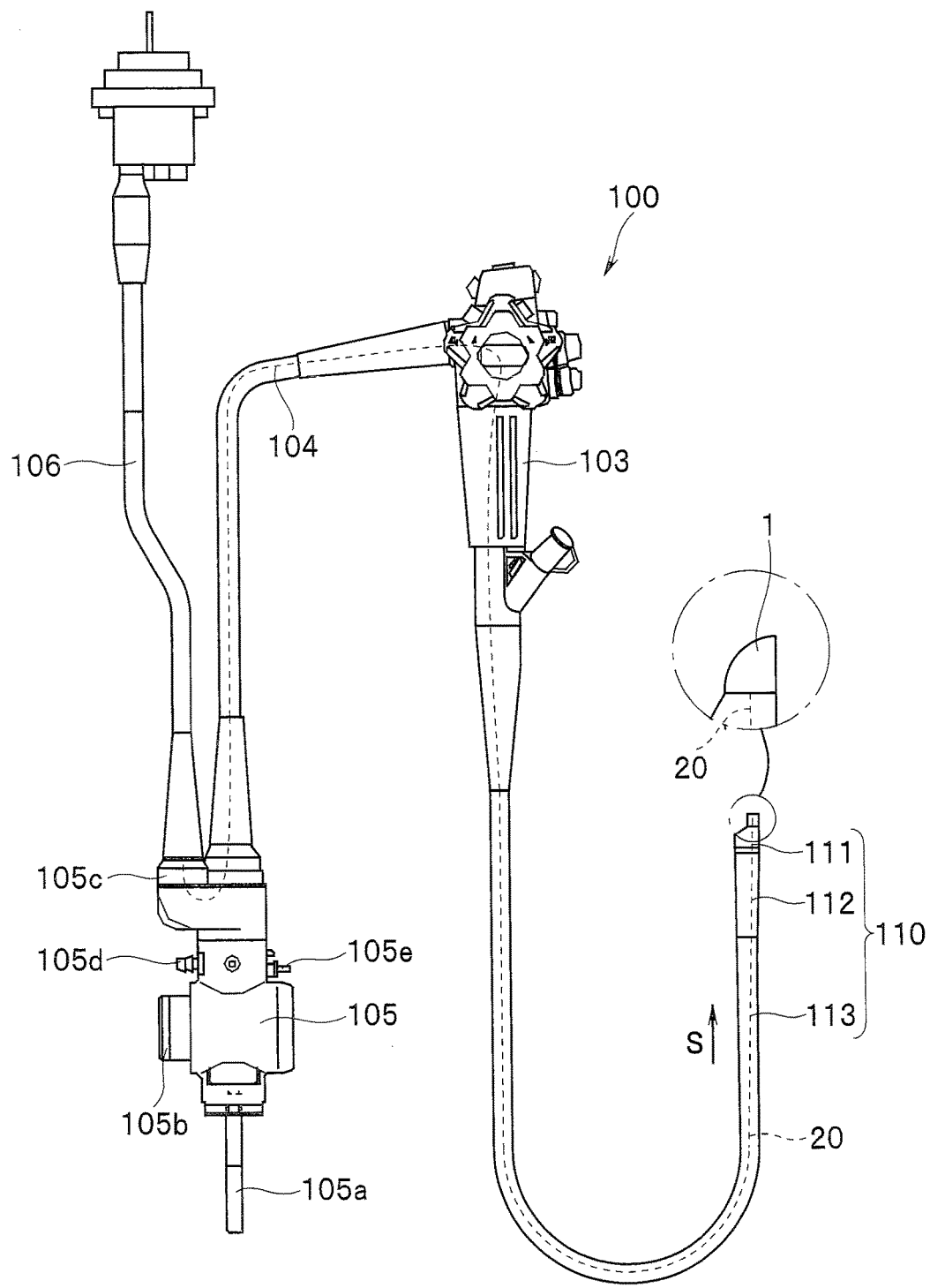
FIG. 1 is a diagram illustrating an example of an outer appearance of an ultrasound endoscope in which an ultrasound transducer according to a first embodiment is provided.

Embodiments of the present invention will be described below with reference to the drawings. It should be noted that the drawings are schematic ones and, e.g., a relationship between a thickness and a width of each member and ratios in thickness among the respective members are different from actual ones, and it should be understood that parts that are different in dimensional relationship and ratio depending on the drawings are included in the drawings.

FIG. 1 is a diagram illustrating an example of an outer appearance of an ultrasound endoscope in which an ultrasound transducer according to the present embodiment is provided.

As illustrated in FIG. 1, a major part of an ultrasound endoscope 100 includes an elongated insertion portion 110 to be inserted into a subject/object, an operation portion 103 provided at a proximal end in an insertion direction S of the insertion portion 110, a flexible universal cord 104 extending from the operation portion 103, and a connector 105 provided at an end of the extension of the universal cord 104.

At the connector 105, a light source connector 105a, an electric connector 105b, an ultrasound connector 105c, a suction pipe sleeve 105d and an air/water feeding pipe sleeve 105e are provided.

A non-illustrated light source apparatus configured to supply illuminating light is detachably attachable to the light source connector 105a, and a non-illustrated video processor configured to perform various signal processing is detachably attachable to the electric connector 105b via a non-illustrated image pickup cable.

Also, an ultrasound cable 106 to be connected to a non-illustrated ultrasound observation apparatus is detachably attachable to the ultrasound connector 105c, a non-illustrated suction pump is detachably attachable to the suction pipe sleeve 105d via a non-illustrated suction tube, and furthermore, a non-illustrated water feeding tank is detachably attachable to the air/water feeding pipe sleeve 105e via a non-illustrated air/water feeding tube.

The insertion portion 110 includes a distal end portion 111, a bending portion 112 configured to be bendable, for example, upward/downward and leftward/rightward, and a flexible tube portion 113 having a long length and flexibility, which are provided so as to be continuous with one another in this order from the distal end side in the insertion direction S.

Inside the distal end portion 111, a known convex-type ultrasound transducer 1 is provided.

An ultrasound signal transmission cable 20 extending from the ultrasound transducer 1 is inserted through the insertion portion 110, operation portion 103, universal cord 104, connector 105, and an end of the extension of the ultrasound signal transmission cable 20 is electrically connected to the ultrasound cable 106 at the ultrasound connector 105c.

Here, inside the distal end portion 111, an image pickup unit and an illumination unit (both not illustrated) are provided.

Also, in an outer surface of the distal end portion 111, a nozzle (not illustrated) of an air/water feeding conduit is provided, and respective distal ends in the insertion direction S of, e.g., a forward water feeding conduit and a treatment instrument insertion channel (both not illustrated) open.

Next, a configuration of the ultrasound transducer 1 in FIG. 1 and a configuration of connection of the ultrasound signal transmission cable 20 to the ultrasound transducer 1 will be described with reference to FIGS. 2 to 6.

Figure 2:
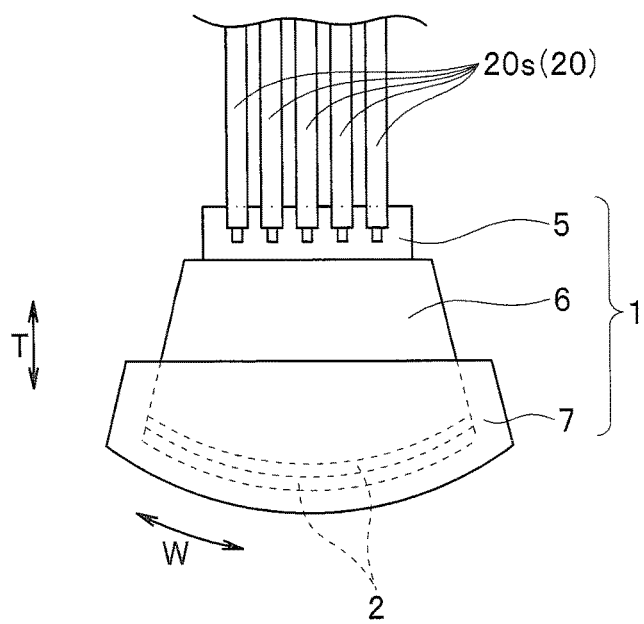
FIG. 2 is a diagram schematically illustrating a state in which an ultrasound signal transmission cable is electrically connected to the ultrasound transducer in FIG. 1.
Figure 3:
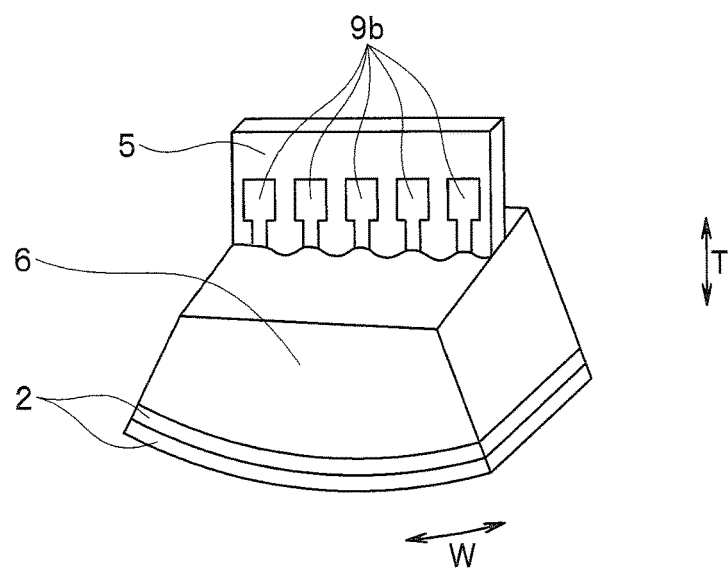
FIG. 3 is a perspective view illustrating the ultrasound transducer in FIG. 2 with a lens and the ultrasound signal transmission cable omitted.
Figure 4:
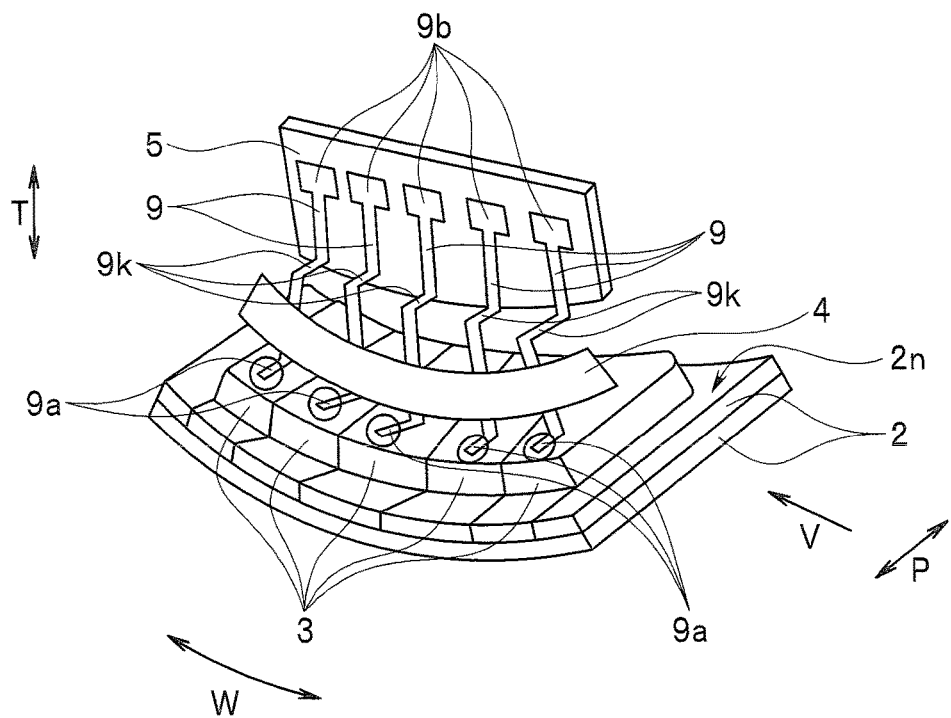
FIG. 4 is a perspective view illustrating the ultrasound transducer in FIG. 3 with a backing material frame and a backing material omitted.

FIG. 2 is a diagram schematically illustrating a state in which an ultrasound signal transmission cable is electrically connected to the ultrasound transducer in FIG. 1, and FIG. 3 is a perspective view of the ultrasound transducer in FIG. 2 with a lens and the ultrasound signal transmission cable omitted, and FIG. 4 is a perspective view of the ultrasound transducer in FIG. 3 with a backing material frame and a backing material omitted.

Figure 5:
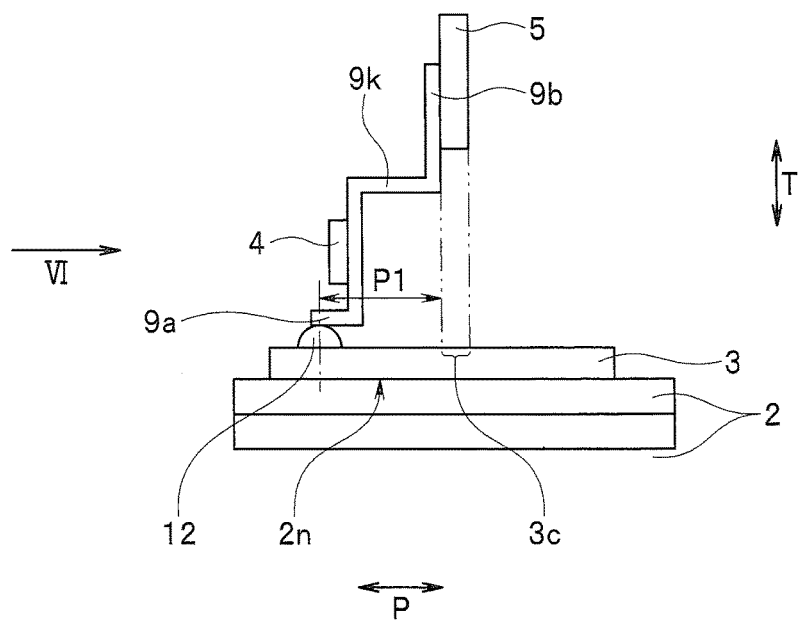
FIG. 5 is a side view of the ultrasound transducer in FIG. 4 as viewed in the V direction in FIG. 4.
Figure 6:
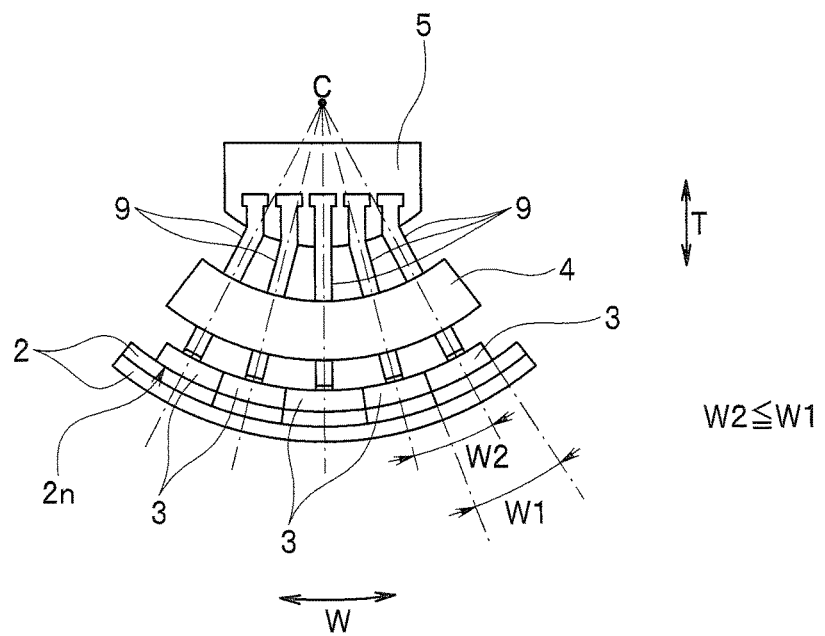
FIG. 6 is a front view of the ultrasound transducer in FIG. 5 as viewed in the VI direction in FIG. 5.

Also, FIG. 5 is a side view of the ultrasound transducer in FIG. 4 as viewed in the V direction in FIG. 4, and FIG. 6 is a front view of the ultrasound transducer in FIG. 5 as viewed in the VI direction in FIG. 5.

As illustrated in FIGS. 2 to 6, the ultrasound transducer 1 is of a convex-type as described above, and thus, includes two acoustic matching layers 2 having a curvature center C and bends with a predetermined curvature.

A layer positioned on the side of the curvature center of the two acoustic matching layers 2 is divided into a plurality of divisional layers in the form of an array. Also, in FIGS. 4 and 6, for ease of illustration, the number of divisional acoustic matching layers 2 is five.

Also, as illustrated in FIGS. 4 to 6, on an inner face 2n on the side of the curvature center C of the acoustic matching layer 2 divided into a plurality of divisional layers in the form of an array, a plurality of divisional piezoelectric elements 3 in the form of an array with a predetermined arrangement pitch W1, the plurality of divisional piezoelectric elements 3 bending with a curvature center C that is the same as the curvature center of the two acoustic matching layers 2, are provided.

Also, on each piezoelectric element 3, a non-illustrated GND electrode is provided on the acoustic matching layer 2 side, and a non-illustrated signal electrode is provided on the side opposite to the acoustic matching layer 2 side, and the piezoelectric elements 3 are each configured to, upon application of a voltage via the two electrodes, radiate ultrasound to an area to be examined via the acoustic matching layers 2 and a later-described lens 7 (see FIG. 2) and receive reflected sound from the area to be examined, and are formed by, for example, firing ceramic, and arranged in a convex shape.

Here, the plurality of piezoelectric elements 3 and the piezoelectric element 3-side layer of the two acoustic matching layers 2 are both divided in an array with the arrangement pitch W1, and for ease of illustration, as with the acoustic matching layer 2, a case where there are five divisional piezoelectric elements 3 is illustrated as an example; however, in reality, generally, there are several hundreds of divisional piezoelectric elements 3 and divisional acoustic matching layers 2 for provision of a high-definition ultrasound image.

Furthermore, as illustrated in FIGS. 4 to 6, respective one ends 9a of a plurality of wirings 9 are electrically connected to the signal electrodes on the plurality of piezoelectric elements 3, respectively, by, e.g., solder 12.

Here, the respective one ends 9a are electrically connected to respective centers in a bending direction W of the respective piezoelectric elements 3.

Furthermore, as illustrated in FIGS. 4 and 5, a position at which the respective one ends 9a are connected to the respective piezoelectric elements 3 are located off a position 3c at which a later-described substrate 5 planarly overlaps the respective piezoelectric elements 3 in a depth direction P of the respective piezoelectric elements 3 and the acoustic matching layers 2.

Also, the plurality of wirings 9 are bare wires that are each not covered by an insulating member but lets a conductive material be exposed for reduction in pitch of the respective piezoelectric elements 3, and each include, for example, a wire with an outer periphery silver-plated.

Also, each wiring 9 includes an ultrafine wire having an outer diameter of no more than 0.05 mm. Furthermore, an example in which the number of wirings 9 is five is indicated in line with the number of piezoelectric elements 3.

Also, as illustrated in FIGS. 4 and 5, the respective other ends 9b of the wirings 9 each include, for example, an insulating member, and are electrically connected to the substrate 5 positioned with a sufficient space from the plurality of piezoelectric elements 3 in a later-described direction T.

FIGS. 2 to 6 indicate a case where the respective other ends 9b of the wirings 9 are formed integrally with the substrate 5, as an example.

Also, in a surface of the substrate 5 on which the other ends 9b are formed, non-illustrated GND wiring lands are formed. Furthermore, a distance from the substrate 5 to the piezoelectric elements 3 in the direction T is set to a distance enough to prevent ultrasound radiated to the curvature center C side from the plurality of piezoelectric elements 3 from being reflected by the substrate 5.

As illustrated in FIG. 2, end portions of a plurality of signal wires 20s included in the ultrasound signal transmission cable 20 via which at least power and electric signals are transmitted/received to/from the respective piezoelectric elements 3 are electrically connected to the respective other ends 9b.

Here, an example in which the number of the plurality of signal wires 20s is five is also indicated in line with the number of the respective wirings 9. Also, as described above, the substrate 5 is positioned off the position at which the respective one ends 9a are connected to the respective piezoelectric elements 3, in the depth direction P.

As illustrated in FIG. 6, the plurality of wirings 9 extend radially with reference to the curvature center C in the direction T in which the substrate 5 and the plurality of piezoelectric elements 3 are connected because the piezoelectric elements 3 are arranged in a convex shape, and as illustrated in FIGS. 4 and 5, each include a flexed portion 9k flexed, for example, in a crank-like shape at a position partway thereof.

Here, each flexed portion 9k is formed between a later-described holding member 4 (see FIGS. 4 to 6) and the substrate 5.

Also, although in FIGS. 4 and 5, the respective flexed portions 9k flex at 90° in two areas so as to have a crank-like shape, the present invention is not limited to this case and the flexed portions 9k may gently bend in two areas to form a crank-like shape.

Also, as illustrated in FIGS. 4 to 6, at a position partway of the plurality of wirings 9, on the respective one ends 9a side relative to the respective flexed portions 9k, a holding member 4 including, for example, an insulating material and having a shape that bends with a curvature center C that is the same as the curvature center of the acoustic matching layers 2 is provided, for example, integrally with the wirings 9.

As a result of the holding member 4 having a curvature center C that is the same as the curvature center of the acoustic matching layers 2, the flexed shapes of the respective flexed portions 9k are identical to one another, and workability in flexing the respective wirings 9 and the flexed shapes of the respective flexed portions 9k are easily stabilized.

As illustrated in FIG. 6, the holding member 4 is configured to hold the plurality of wirings 9 at a regular pitch W2 (W2≤W1) that is equal to or smaller than the arrangement pitch W1 of the plurality of piezoelectric elements 3 to prevent displacement of the respective wirings 9 and thereby prevent the respective wirings 9 from coming into contact with one another, as a result of the holding member 4 being positioned on the flexed portion 9k side relative to the plurality of piezoelectric elements 3 in the direction T.

Also, the holding member 4 holds the plurality of wirings 9 to be shifted by ½ of the pitch from the arrangement pitch W1 of the plurality of piezoelectric elements 3 and thereby hold the plurality of wirings 9 so that the respective one ends 9a of the wirings 9 are electrically connected to respective centers in the bending direction W of the respective piezoelectric elements 3.

Also, as illustrated in FIG. 3, the plurality of piezoelectric elements 3, parts of the respective one ends 9a of the wirings 9, the parts being connected to the respective piezoelectric elements 3, the holding member 4, and the flexed portion 9k are covered by a backing material frame 6.

Here, the backing material frame 6 includes, for example, a glass epoxy resin. The backing material frame 6 is formed in a frame shape having a rectangular shape in a planar view, by opposed two end boards and opposed two side boards. Also, the inside of the backing material frame 6 is charged with a non-illustrated backing material.

Furthermore, as illustrated in FIG. 2, a half part on the side of the acoustic matching layer 2 of the backing material frame 6 and an outer periphery of the acoustic matching layers 2 are covered by the lens 7.

As described above, the present embodiment indicates that the holding member 4 configured to hold the plurality of wirings 9 with the regular pitch W2 (W2≤W1) that is equal to or smaller than the arrangement pitch W1 of the plurality of piezoelectric elements 3 is provided at a position partway of the plurality of wirings 9 extending radially in the direction T between the respective one ends 9a and the respective flexed portions 9k.

Therefore, even if the plurality of wirings 9 in a bare-wire state in which the conductive material is exposed is deformed by an external force, displacement of the respective wirings 9 can be prevented by the holding member 4 and thus the respective wirings 9 can reliably be prevented from coming into contact with each other, facilitating connection of the respective wirings 9 to the plurality of piezoelectric elements 3.

Also, the present embodiment indicates that the crank-shaped flexed portions 9k are formed at respective position partway of the respective wirings 9 in the direction T between the holding member 4 and the respective other ends 9b.

Furthermore, the present embodiment indicates that the position at which the respective one ends 9a of the wirings 9 are connected to the respective piezoelectric elements 3 is located off in the depth direction P from the position 3c at which the substrate 5 planarly overlaps the respective piezoelectric elements 3.

Also, the present embodiment indicates that the respective flexed portions 9k are located at respective positions partway of the respective wirings 9 in the direction T between the holding member 4 and the substrate 5.

Therefore, after connection of the respective one ends 9a to the respective piezoelectric elements 3, even if an external force is provided to the respective wirings 9, for example, even if a tensile force is provided in the direction T, the provided force is reduced and absorbed by the respective flexed portions 9k of the respective wirings 9, and thus, the respective wirings 9 can be prevented from coming into contact with one another, and in the connection work, the respective wirings 9 can easily be connected to the plurality of piezoelectric elements 3.

According to the above, an ultrasound transducer 1 including a configuration that prevents a plurality of wirings 9 connecting a plurality of piezoelectric elements 3 and a substrate 5 from coming into contact with one another and facilitates electrical connection of the plurality of wirings 9 to a plurality of piezoelectric elements 3, and an ultrasound endoscope 100 can be provided.

Figure 7:
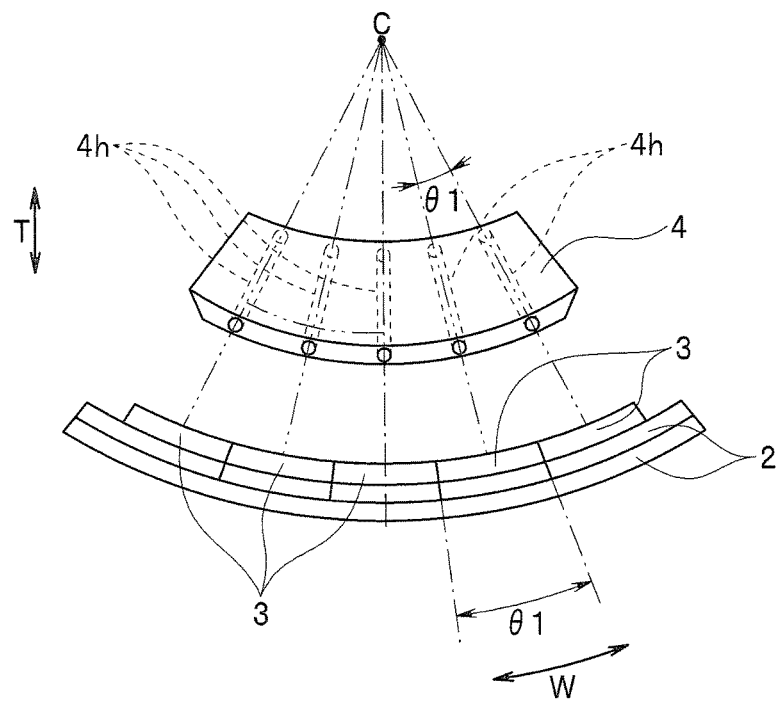
FIG. 7 is a diagram schematically illustrating a modification in which insertion holes configured to allow respective wirings to be inserted therethrough are formed in a holding member in FIG. 4, together with piezoelectric elements and acoustic matching layers.

A modification will be indicated below with reference to FIGS. 7 to 10. FIG. 7 is a diagram schematically illustrating a modification in which insertion holes configured to allow respective wirings to be inserted are formed in the holding member in FIG. 4, together with piezoelectric elements and acoustic matching layers, and FIG. 8 is a diagram schematically illustrating a state in which a plurality of wirings are inserted through the insertion holes in FIG. 7 and fixed to the holding member.

Figure 8:
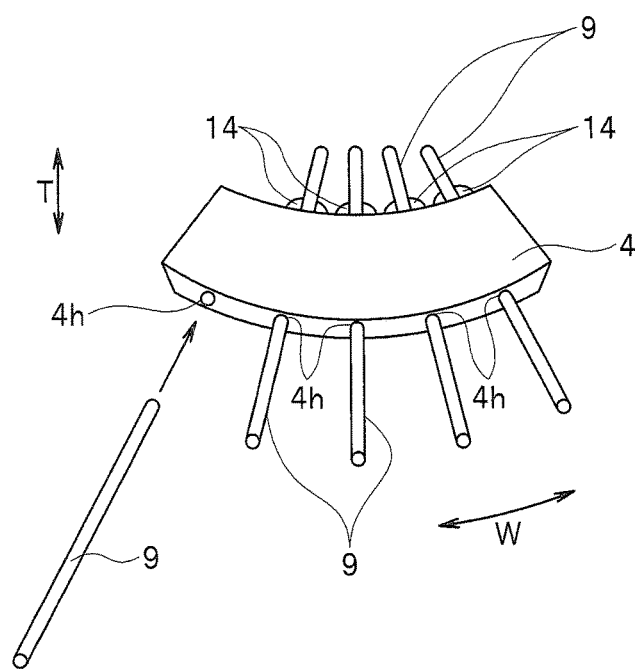
FIG. 8 is a diagram schematically illustrating a state in which a plurality of wirings are inserted through the insertion holes in FIG. 7 and fixed to the holding member.
Figure 9:
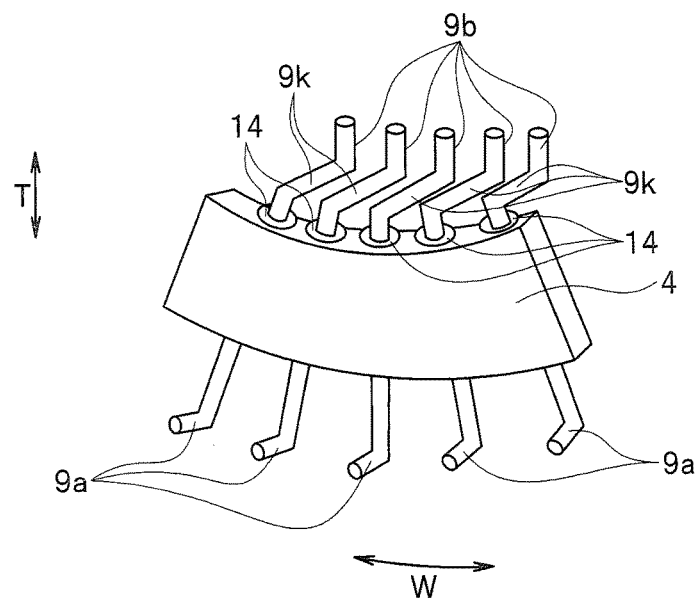
FIG. 9 is a diagram schematically illustrating a state in which a flexed portion is formed in each of the plurality of wirings inserted through the insertion holes and fixed to the holding member in FIG. 8.
Figure 10:
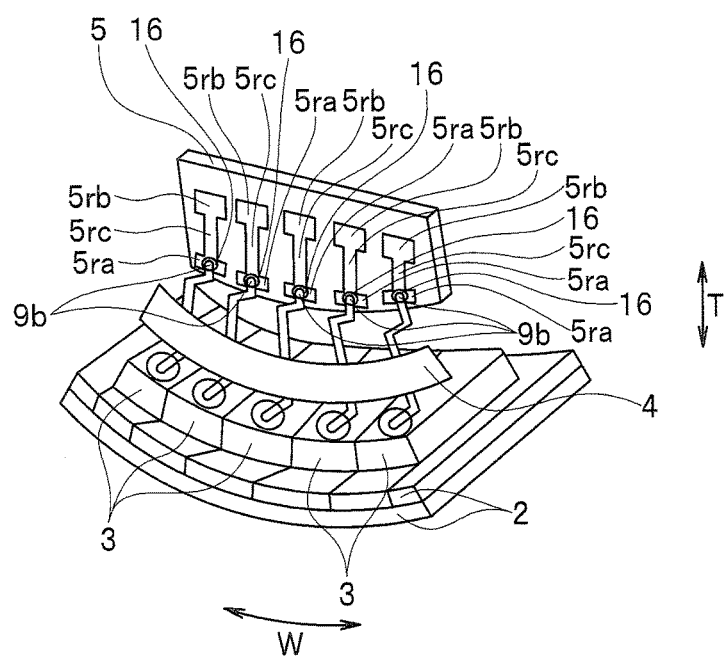
FIG. 10 is a diagram schematically illustrating a state in which respective one ends of the wirings in FIG. 9 are electrically connected to the respective piezoelectric elements and the respective other ends of the wirings are electrically connected to a substrate.

Also, FIG. 9 is a diagram schematically illustrating a state in which a flexed portion is formed in each of the plurality of wirings inserted through the insertion holes and fixed to the holding member in FIG. 8, and FIG. 10 is a diagram schematically illustrating a state in which respective one ends of the wirings in FIG. 9 are electrically connected to the respective piezoelectric elements and the respective other ends of the wirings are electrically connected to a substrate.

As illustrated in FIG. 7, it is possible that: a holding member 4 is formed separately from a plurality of wirings 9; and insertion holes 4h extending radially with reference to a curvature center C are formed along a direction T in the holding member 4. Here, the respective insertion holes 4h are formed at an angle pitch θ1 that is the same as an angle pitch θ1 of the respective piezoelectric elements 3.

Also, as illustrated in FIG. 8, the plurality of wirings 9 formed separately from the holding member 4 are inserted through the respective insertion holes 4h, and the respective wirings 9 are each fixedly attached to the holding member 4 via, e.g., an adhesive 14.

As illustrated in FIG. 9, respective flexed portions 9k are formed as a result of parts on the side of the respective other ends 9b of the respective wirings 9 relative to the holding member 4 being collectively flexed, and subsequently, as illustrated in FIG. 10, respective one ends 9a are electrically connected to the respective piezoelectric elements 3, and the respective other ends 9b are electrically connected to respective wiring lands 5ra of a substrate 5 via, e.g., solder 16.

In the substrate 5, the respective wiring lands 5ra are electrically continuous with respective wiring lands 5rb via respective wiring lands 5rc, and respective end portions of a plurality of signal wires 20s included in an ultrasound signal transmission cable 20 are electrically connected to the respective wiring lands 5rb.

According to such configuration as above, the respective wirings 9 are formed separately from the holding member 4 and the substrate 5, and thus, a material of the respective wirings 9 can freely be selected, and if a highly-rigid material is used, flexed shapes of the respective flexed portions 9k after the formation can more easily be stabilized, and the subsequent workability is enhanced.

Other effects are the same as those of the present embodiment described above.

Figure 11:
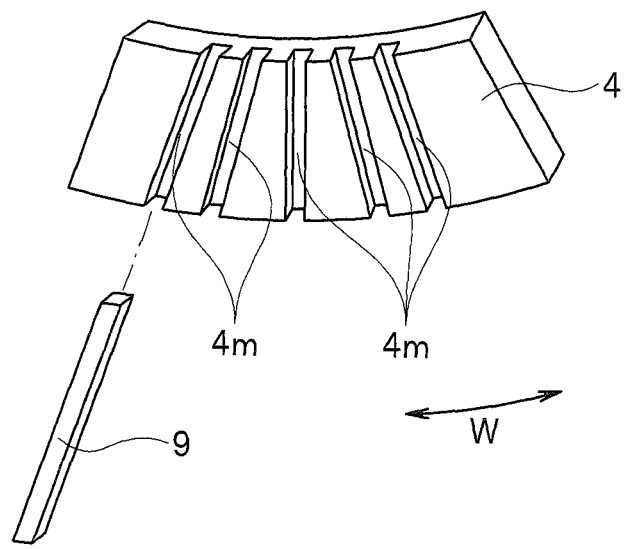
FIG. 11 is a diagram schematically illustrating a modification in which the wirings in FIG. 10 each include a rectangular wire and recess portions configured to allow the rectangular wires to be inserted therethough are formed in a holding member.

Also, another modification will be described below with reference to FIG. 11. FIG. 11 is a diagram schematically illustrating a modification in which the wirings in FIG. 10 each include a rectangular wire and recess portions configured to allow the rectangular wire to be inserted therethrough are formed in a holding member.

As illustrated in FIG. 11, each wiring 9 may include a rectangular wire, and each insertion hole illustrated in FIGS. 7 to 10 may be a recess portion 4m configured to allow a rectangular wire to be inserted therethrough. As in the present embodiment, in each rectangular wire, also, a flexed portion 9k is formed after the rectangular wire is fixed to the corresponding recess portion 4m.

According to such configuration as above, although in the modification illustrated FIGS. 7 to 10, the insertion holes 4h configured to allow the respective wirings 9 to be inserted therethrough are formed in the holding member 4, forming of the recess portions 4m is easier in working than forming of the insertion holes 4h, enabling reduction in manufacturing cost.

The respective wirings 9 may be fixed to the holding member 4 via, e.g., an adhesive material. In this case, the manufacturing costs may further be reduced.

Furthermore, an example of a manufacturing method in which the substrate, the respective wirings and the holding member in FIG. 4 are integrally formed will be indicated below with reference to FIGS. 12 to 14.

Figure 12:
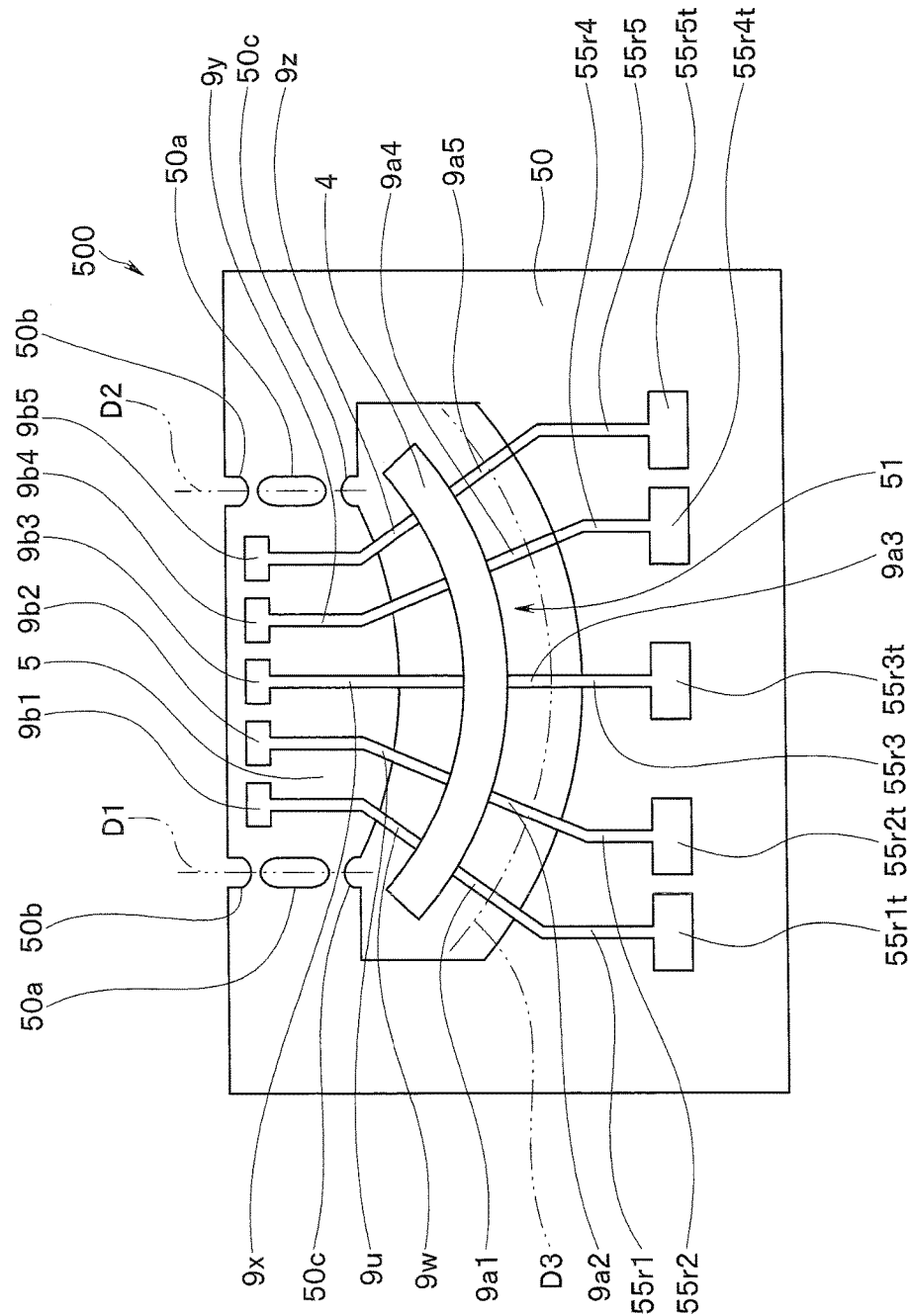
FIG. 12 is a diagram schematically illustrating a modification in which the substrate, the respective wirings and the holding member in FIG. 4 are formed integrally with a waste substrate.
Figure 13:
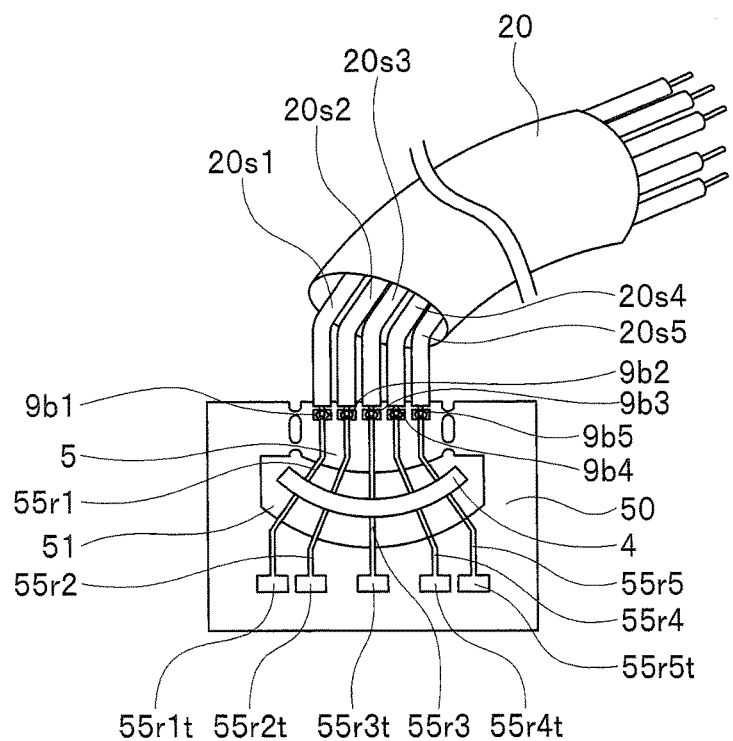
FIG. 13 is a diagram illustrating a state in which respective one end portions of a plurality of signal wires are electrically connected to the respective other ends of the wirings on the substrate in FIG. 12.
Figure 14:
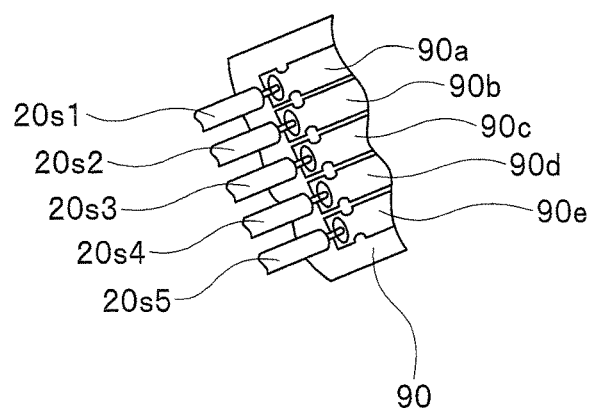
FIG. 14 is a diagram illustrating a state in which the respective other end portions of the plurality of signal wires in FIG. 13 are electrically connected to wiring lands of a flexible substrate in a connector of an endoscope.

FIG. 12 is a diagram schematically illustrating a modification in which the substrate, the respective wirings and the holding member in FIG. 4 are formed integrally with a waste substrate, FIG. 13 is a diagram illustrating a state in which respective one end portions of a plurality of signal wires are electrically connected to the respective other ends of the wirings on the substrate in FIG. 12, and FIG. 14 is a diagram illustrating a state in which the respective other end portions of the plurality of signal wires in FIG. 13 are electrically connected to wiring lands of a flexible substrate in a connector of an endoscope.

For manufacturing the substrate 5, the respective wirings 9 and the holding member 4 described above, the below-indicated method may be employed.

First, as illustrated in FIG. 12, a structure 500 including a substrate 5, respective wirings 9w, 9u, 9x, 9y, 9z formed integrally with the substrate 5, a holding member 4, a waste substrate 50, respective wirings 55r1 to 55r5 that are mounted on the waste substrate 50 and communicate with the respective wirings 9w, 9u, 9x, 9y, 9z, and check lands 55r1t, 55r2t, 55r3t, 55r4t, 55r5t that are mounted on the waste substrate 50 and communicate with the respective wirings 55r1 to 55r5 is prepared.

As illustrated in FIG. 12, a hole 51 is formed in the waste substrate 50 so as to surround the holding member 4, and cutting holes 50a and cutting grooves 50b, 50c are formed between the waste substrate 50 and the substrate 5.

Next, as illustrated in FIG. 13, respective one ends of a plurality of signal wires 20s1, 20s2, 20s3, 20s4, 20s5 included in an ultrasound signal transmission cable 20 are electrically connected to respective end portions 9b1, 9b2, 9b3, 9b4, 9b5 via, e.g., solder. Here, the respective soldered parts are protected and fixed via, e.g., an adhesive as necessary.

Subsequently, electric continuity between the check lands 55r1t to 55r5t and the respective other ends of the signal wires 20s1 to 20s5 is checked using a tester to check if each of the signal wires 20s1 to 20s5 is connected to any of the wirings 9w to 9z and check electric conduction of the respective soldered parts.

Next, as illustrated in FIG. 14, the respective other ends of the signal wires 20s1 to 20s5 are electrically connected via, e.g., solder to respective wiring lands 90a, 90b, 90c, 90d, 90e of a flexible substrate 90 provided inside a connector 105 of an ultrasound endoscope 100.

Subsequently, using a tester, electrical continuity between the check lands 55r1t to 55r5t and the respective wiring lands 90a to 90e is checked using a tester to check whether or not there are erroneous wiring, disconnection of any of the soldered parts and/or short-circuits.

Lastly, the cutting holes 50a and the cutting grooves 50b and 50c are cut apart along straight lines D1 and D2, and the waste substrate 50 and the wirings 55r1 to 55r56 are cut off along a circular-arc line D3. As a result, the substrate 5, the respective wirings 9 and the holding member 4 such as illustrated in FIG. 4 are formed.

According to such manufacturing method as above, when the respective one ends of the signal wires 20s1 to 20s5 are connected to the respective other ends 9b1 to 9b5, because the substrate 5 and the waste substrate 50 are disposed so as to surround the respective wirings 9w to 9z, a strength of the connection can be increased, and workability is enhanced because an external force is less likely to be applied to the respective wirings 9w to 9z.

Furthermore, since the large check lands 55r1t to 55r5t are provided in the waste substrate 50, wiring arranging work for the signal wires 20s1 to 20s5 is easier than that performed using the respective other ends 9b1 to 9b5, which are small and have a narrow arrangement pitch, enabling connection positions of the signal wires 20s1 to 20s5 to be reliably checked and thus enabling enhancement in workability and quality of the ultrasound transducer 1.

Second Embodiment

Figure 15:
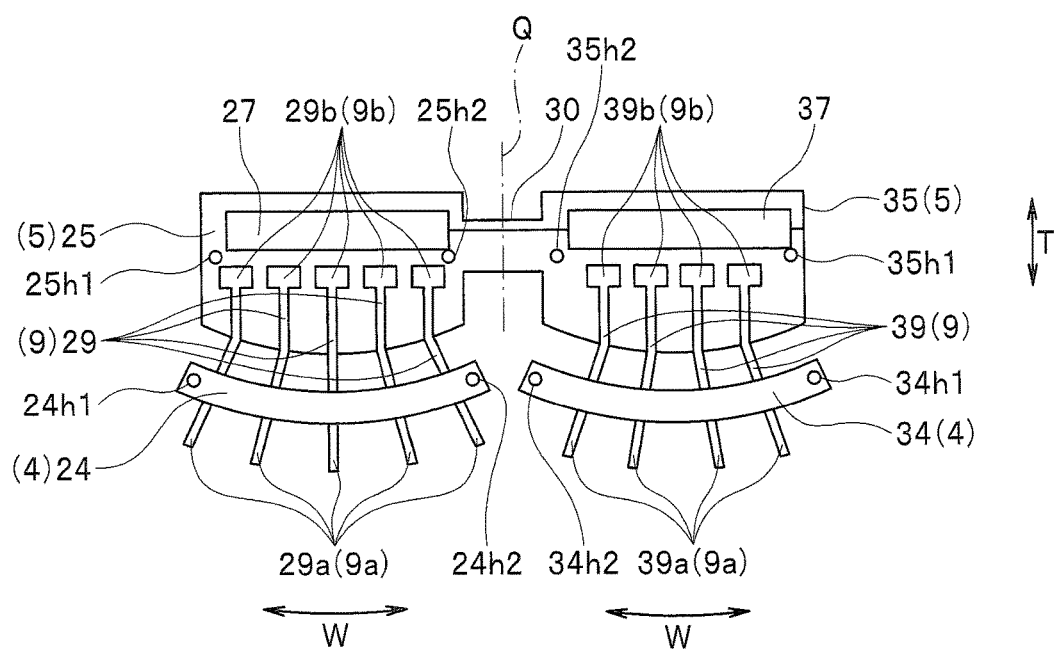
FIG. 15 is an exploded view of a substrate, respective wirings and a holding member in an ultrasound transducer according to a second embodiment.
Figure 16:
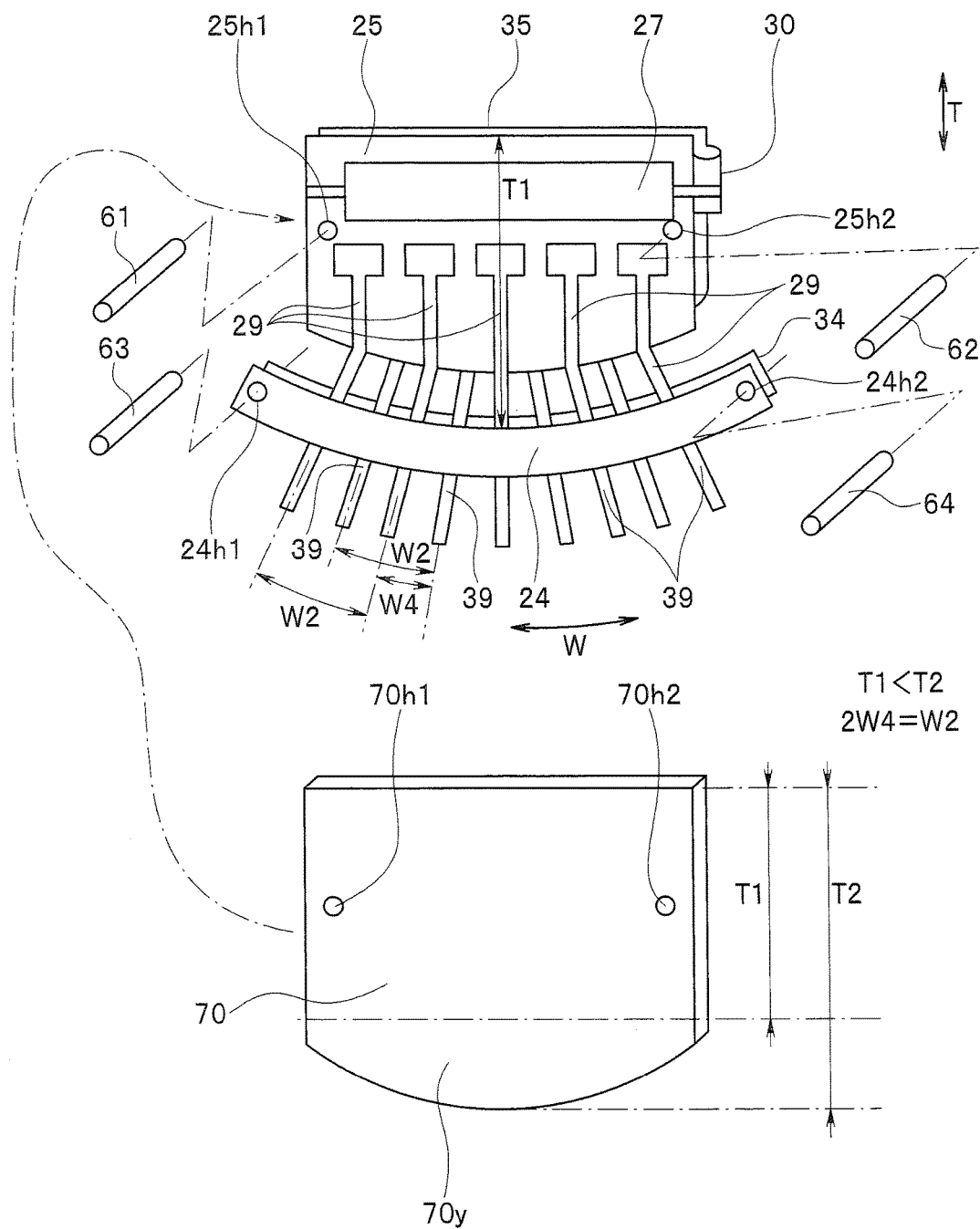
FIG. 16 is a perspective view illustrating the substrate, the respective wirings and the holding member in FIG. 15 as assembled, together with a reinforcing plate.

FIG. 15 is an exploded view of a substrate, respective wirings, a holding member in an ultrasound transducer according to the present embodiment, and FIG. 16 is a perspective view of the substrate, the respective wirings and the holding member in FIG. 15 as assembled, together with a reinforcing plate.

A configuration of the ultrasound transducer according to the second embodiment is different from that of the ultrasound transducer according to the first embodiment illustrated in FIG. 1 to FIG. 6 described above in that the substrate includes a pair of substrates, each wiring includes a pair of wirings, and the holding member includes a pair of holding members, respectively. Therefore, components that are similar to those of the first embodiment will be provided with reference numerals that are the same as those of the first embodiment, and description thereof will be omitted.

As illustrated in FIGS. 15 and 16, in the present embodiment, a substrate 5 includes a first substrate 25 and a second substrate 35. Also, a plurality of wirings 9 include a plurality of first wirings 29 including the respective other ends 29b electrically connected to the first substrate 25, and a plurality of second wirings 39 including the respective other ends 39b electrically connected to the second substrate 35.

Furthermore, a holding member 4 includes a first holding member 24 provided at a position partway of the plurality of first wirings 29, the first holding member 24 being configured to hold the first wirings 29 at a regular pitch W2 that is equal to or smaller than an arrangement pitch W1 of a plurality of piezoelectric elements 3, and a second holding member 34 provided at a position partway of the plurality of second wirings 39, the second holding member 34 being configured to hold the second wirings 39 at the regular pitch W2 that is equal to or smaller than the arrangement pitch W1 of the plurality of piezoelectric elements 3.

Here, the first substrate 25 and the second substrate 35 have a same size and a same shape, and are joined to each other at a joining portion 30.

Also, the first substrate 25 and the second substrate 35 are provided so as to be continuous with each other and have a same potential as a result of a GND terminal 27 mounted on a surface of the first substrate 25 and a GND terminal 37 mounted on a surface of the second substrate 35 being connected via the joining portion 30 by a wiring.

Furthermore, as illustrated in FIG. 16, the second substrate 35 is folded back at 180° along a fold line Q via the joining portion 30, and a back face of the second substrate 35 is thereby positioned so as to overlap a back face of the first substrate 25.

In the first substrate 25, positioning holes 25h1, 25h2 are formed, and in the second substrate 35, positioning holes 35h1, 35h2 are formed, and as illustrated in FIG. 16, a positioning pin 61 is inserted through the positioning holes 25h1, 35h1, and a positioning pin 62 is inserted through the positioning holes 25h2, 35h2, whereby the first substrate 25 and the second substrate 35 having the same shape exactly overlap each other. Also, as illustrated in FIG. 16, the back faces of the first substrate 25 and the second substrate 35 are bonded and fixed to each other.

Also, as with the wirings 9 in the first embodiment described above, the first wirings 29 and the second wirings 39 are each formed radially with reference to a curvature center C with a pitch W2 that is the same as the pitch of the wirings 9 in the first embodiment described above, the respective pitches W4 of the first wirings 29 and the second wirings 39 are shifted from each other by ½ of the pitch (2W4=W2).

As illustrated in FIG. 16, when the back face of the first substrate 25 and the back face of the second substrate 35 are bonded to each other, the first wirings 29 and the second wirings 39 are flexed outward at respective positions partway thereof in a direction T so as to be directed in respective directions away from each other, and are positioned in a staggered manner in a bending direction W, and are held in the staggered manner by the first holding member 24 and the second holding member 34, respectively. Consequently, the first wirings 29 and the second wirings 39 having the small pitch in the bending direction W are prevented from coming into contact with one another.

The first holding member 24 and the second holding member 34 are provided at respective positions partway of the first wirings 29 and the second wirings 39, respectively, the positions being the same in the direction T, and have a same size and a same shape.

Here, when the back face of the first substrate 25 and the back face of the second substrate 35 are bonded to each other, a back face of the first holding member 24 faces a back face of the second holding member 34. Also, in the first holding member 24, positioning holes $24h1$, $24h2$ are formed, and in the second holding member 34, positioning holes $34h1$, $34h2$ are formed, as illustrated in FIG. 16, a positioning pin 63 is inserted through the positioning holes $24h1$, $34h1$, and a positioning pin 64 is inserted through the positioning holes $24h2$, $34h2$, and the first holding member 24 and the second holding member 34 having the same shape exactly overlap each other.

Next, a manufacturing method for the present embodiment will be described.

First, first wirings 29 and second wirings 39 are flexed outward at respective positions partway thereof so as to extend away from each other.

Next, a joining portion 30 is folded at 180° along a fold line Q so that back faces of a second substrate 35 and a second holding member 34 face back faces of a first substrate 25 and a first holding member 24, respectively, via the joining portion 30.

Subsequently, a positioning pin 61 is inserted through positioning holes $25h1$, $35h1$, and a positioning pin 62 is inserted through positioning holes $25h2$, $35h2$, a positioning pin 63 is inserted through positioning holes $24h1$, $34h1$, and a positioning pin 64 is inserted through positioning holes $24h2$, $34h2$, whereby the second substrate 35 overlaps the first substrate 25 and the second holding member 34 overlaps the first holding member 24.

As a result, the first wirings 29 and the second wirings 39 are neatly positioned in a staggered manner in which the first wirings 29 and the second wirings 39 are shifted from each other by ½ of the pitch. In this state, the back face of the first substrate 25 and the back face of the second substrate 35 are bonded and fixed to each other, and respective one ends $29a$ and respective one ends $39a$ of the respective first wirings 29 and respective second wirings 39 in the staggered manner are electrically connected to signal electrodes of the plurality of piezoelectric elements 3.

According to such configuration as above, the wiring pitch W4 of the first wirings 29 and the second wirings 39 in the bending direction W is smaller by ½ of compared to the pitch W2 of the plurality of wirings 9 in the above-described first embodiment, enabling the wirings to be mounted on the plurality of piezoelectric elements 3 at high density with a simple configuration. Other effects are the same as those of the above-described first embodiment.

A modification will be indicated below. As illustrated in FIG. 16, a reinforcing plate 70 having a length T2 that is longer than a length T1 of the first substrate 25 and the second substrate 35 in a direction T may be interposed between the back face of the first substrate 25 and the back face of the second substrate 35 (T1<T2).

Here, in the reinforcing plate 70, positioning holes $70h1$, $70h2$ configured to allow positioning pins 61, 62 to be inserted therethrough, respectively, are formed, and as a result of the positioning pins 61, 62 being inserted through the positioning holes $70h1$, $70h2$, the reinforcing plate 70 is positioned between the substrates 25, 35.

Also, if an adhesive is applied to surfaces of the reinforcing plate 70 that face the respective substrates 25, 35, the respective substrates 25, 35 and the reinforcing plate 70 are easily bonded and fixed to each other. Also, a double-stick tape may be used for bonding the reinforcing plate 70 and the respective substrates 25, 35 to each other.

According to such configuration as above, if the first substrate 25 and the second substrate 35 are each formed in a thin plate-like shape such as a flexible substrate, the reinforcing plate 70 makes the substrates 25, 35 less easily deform.

Furthermore, since the reinforcing plate 70 is formed to be longer than the first substrate 25 and the second substrate 35 in the direction T, as illustrated in FIG. 16, a protruding portion $70y$ can reliably prevent respective areas of the first wirings 29 between the holding member 24 and the respective other ends $29b$ and respective areas of the second wirings 39 between the holding member 34 and the respective other ends $39b$ from coming into contact with one another.

Third Embodiment

Figure 17:
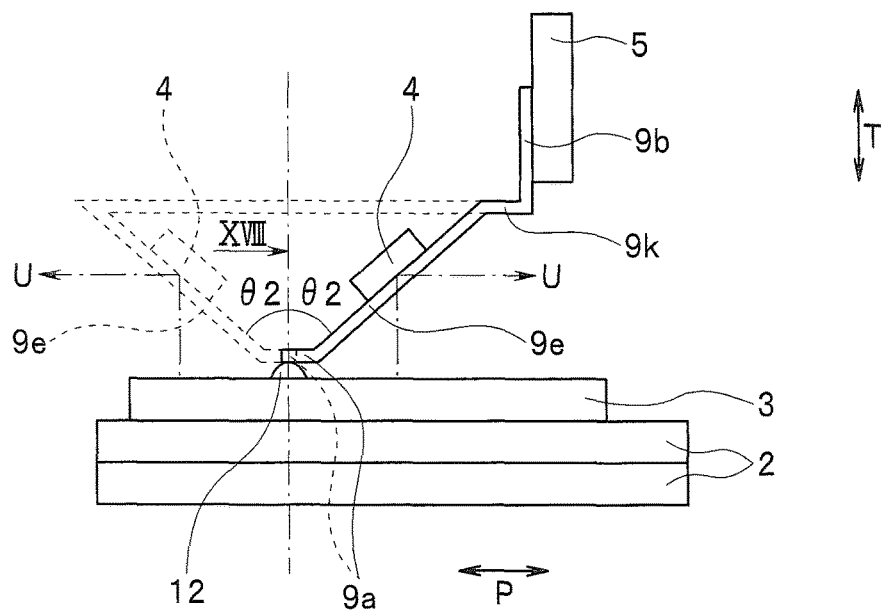
FIG. 17 is a diagram schematically illustrating a substrate, respective wirings and a holding member in an ultrasound transducer according to a third embodiment.

FIG. 17 is a diagram schematically illustrating a substrate, respective wirings and a holding member in an ultrasound transducer according to the present embodiment.

A configuration of the ultrasound transducer according to the third embodiment is different from that of the ultrasound transducer according to the first embodiment illustrated in FIGS. 1 to 6 described above in that a holding member and areas of respective wirings in which the holding member is provided are inclined. Therefore, components that are similar to those of the first embodiment are provided with reference numerals that are the same as those of the first embodiment, and description thereof will be omitted.

As illustrated in FIG. 17, in the present embodiment, a holding member 4 and an area $9e$ of each wiring 9 in which the holding member 4 is provided is inclined at a predetermined angle $\theta2$, more specifically, an angle of within $\theta2=\pm45°$, relative to a direction T. The rest of the configuration is the same as the configuration of the above-described first embodiment.

According to such configuration as above, even if back waves U from respective piezoelectric elements 3 hit the holding member 4, the back waves U are reflected in a depth direction P, and thus, the reflected waves are less likely to be received by the respective piezoelectric elements 3.

This effect is exerted if an angle $\theta2$ of the holding member 4 and the area $9e$ of each wiring 9 is within $\pm45°$ relative to the direction T. The other effects are the same as those of the above-described first embodiment.

Figure 18:
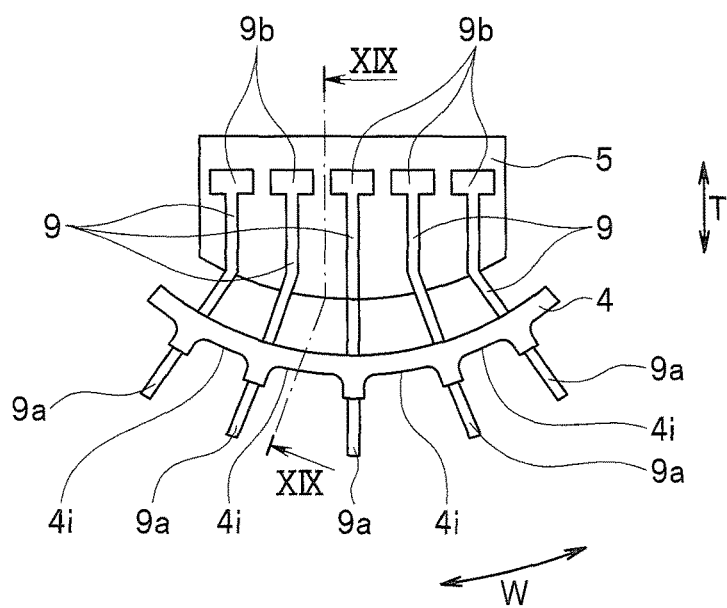
FIG. 18 is a front view of a modification in which recess portions are provided in the holding member in FIG. 17 as viewed in the XVIII direction in FIG. 17.

A modification will be described below with reference to FIGS. 18 and 19. FIG. 18 is a front view of a modification in which recess portions are provided in the holding member in FIG. 17 as viewed in the XVIII direction in FIG. 17, and FIG. 19 is a partial cross-sectional view of the ultrasound transducer along line XIX-XIX in FIG. 18.

Figure 19:
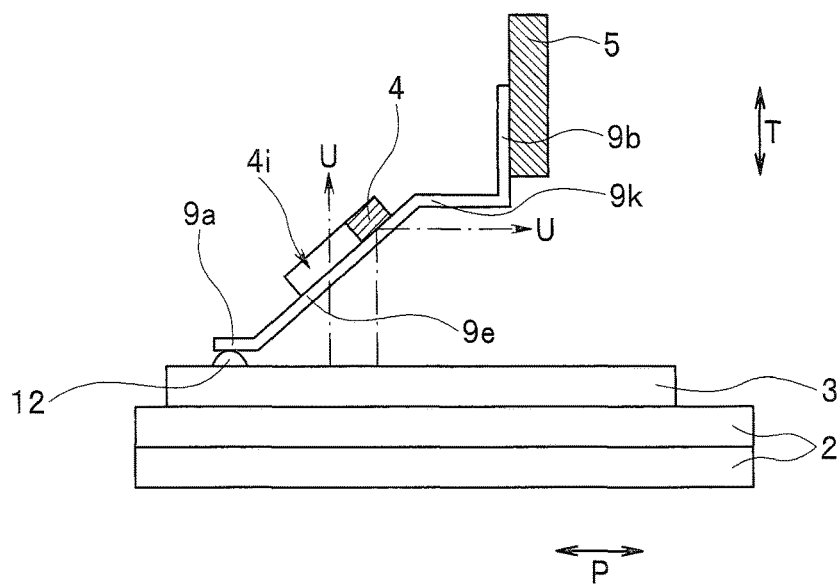
FIG. 19 is a partial cross-sectional view of the ultrasound transducer along line XIX-XIX in FIG. 18.

As illustrated in FIGS. 18 and 19, as in the present embodiment described above, in a holding member 4 inclined at a predetermined angle relative to a direction T together with areas 9e, a plurality of recess portions 4i configured to allow back waves U to pass therethrough, which are ultrasound radiated from a plurality of piezoelectric elements 3, may be found.

More specifically, in each area of the holding member 4, the area being located between adjacent wirings 9 in a bending direction W, a recess portion 4i may be formed. The rest of the configuration is the same as the configuration of the present embodiment described above.

According to such configuration as above, back waves U from the respective piezoelectric elements 3 pass through the holding member 4 via the plurality of recess portions 4i, enabling reduction in generation of reflected waves from the holding member 4.

Figure 20:
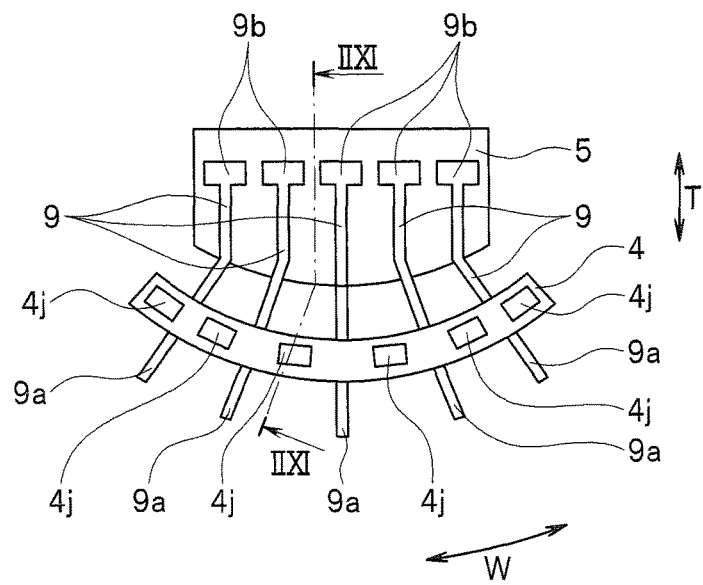
FIG. 20 is a diagram illustrating a modification in which a plurality of holes are formed instead of the plurality of recess portions in the holding member in FIG. 18.

Also, another modification will be indicated below with reference to FIGS. 20 and 21. FIG. 20 is a diagram illustrating a modification in which a plurality of holes are formed instead of the plurality of recess portions in the holding member in FIG. 18, and FIG. 21 is a partial cross-sectional view of an ultrasound transducer along line IIXI-IIXI in FIG. 20.

Figure 21:
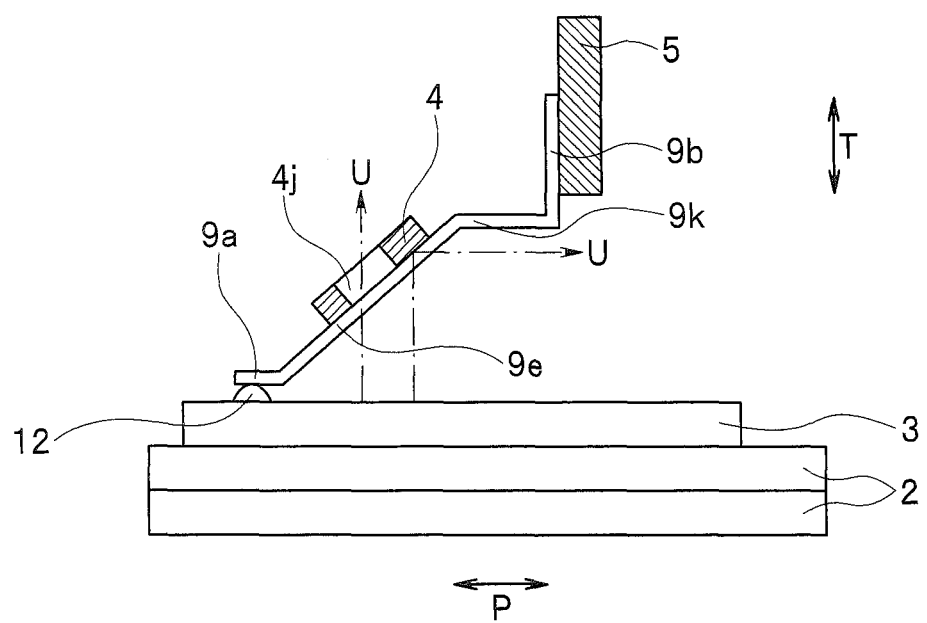
FIG. 21 is a partial cross-sectional view of the ultrasound transducer along line IIXI-IIXI in FIG. 20.

As illustrated in FIGS. 20 and 21, in a holding member 4 inclined at a predetermine angle in a direction T together with areas 9e, a plurality of holes 4j configured to allow back waves U to pass therethrough, which are ultrasound radiated from a plurality of piezoelectric elements 3, may be formed.

More specifically, in each area of the holding member 4, the area being located between adjacent wirings 9 in a bending direction W, a hole 4j may be formed. The rest of the configuration is the same as the configuration of the present embodiment described above.

According to such configuration as above, also, back waves U from the respective piezoelectric elements 3 pass through the holding member 4 via the plurality of holes 4j, enabling reduction in generation of reflected waves from the holding member 4.

An example of a configuration for correction of displacement in a bending direction W when respective one ends 9a of a plurality of wirings 9 are connected to a plurality of piezoelectric elements 3 will be described below with reference to FIGS. 22 and 23.

Figure 22:
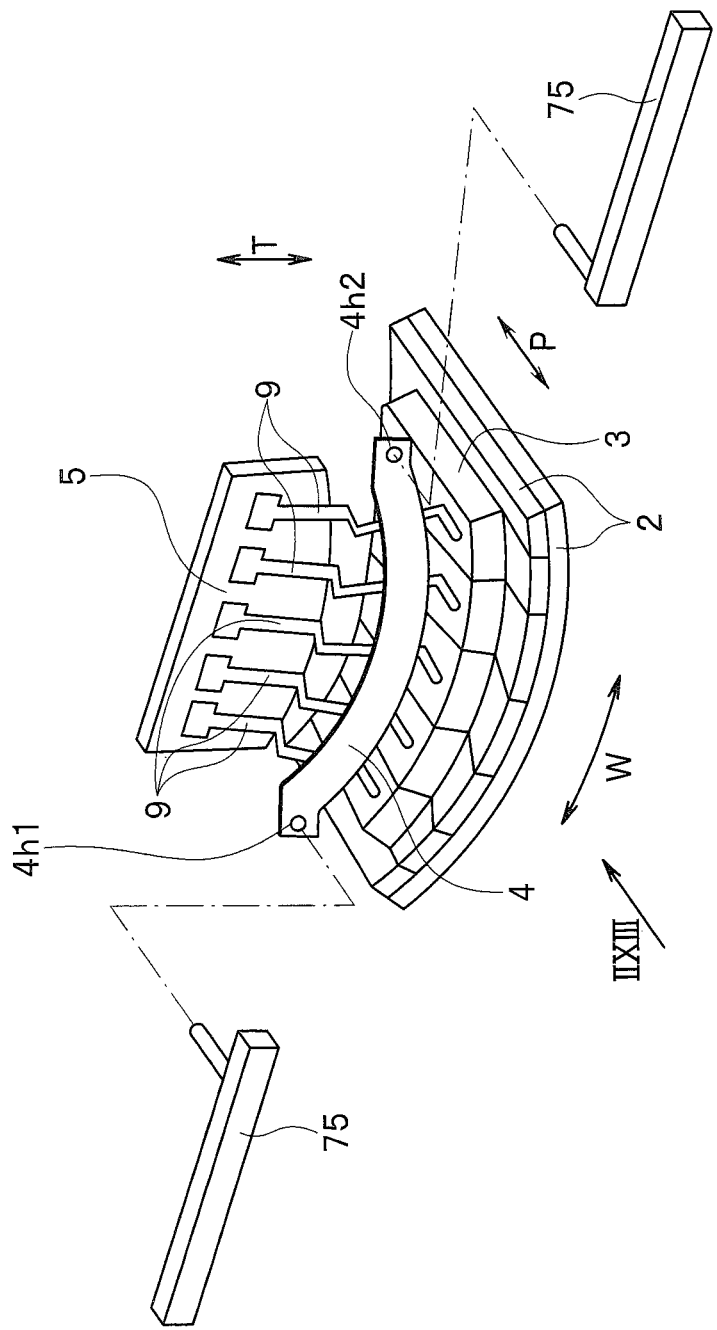
FIG. 22 is a perspective view illustrating a modification in which fitting portions configured to allow adjustment members to be fitted therein are formed in the holding member in FIG. 4.
Figure 23:
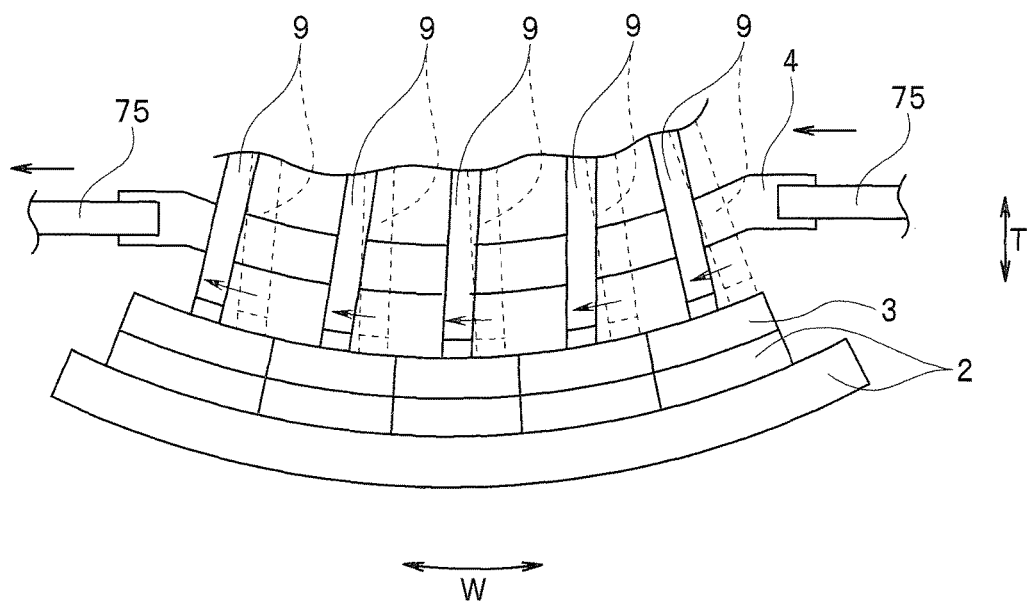
FIG. 23 is a front view of the ultrasound transducer and the adjustment members in FIG. 22 as viewed in the IIXIII direction in FIG. 22.

FIG. 22 is a perspective view illustrating a modification in which fitting portions configured to allow adjustment members to be fitted therein are formed in the holding member in FIG. 4, and FIG. 23 is a front view of the ultrasound transducer and the adjustment member in FIG. 22 as viewed in the IIXIII direction in FIG. 22.

As described above, when respective one ends 9a of a plurality of wirings 9 held with a regular pitch in a bending direction W by a holding member 4 are electrically connected to a plurality of piezoelectric elements 3, in a phase in which the respective one ends 9a are brought into contact with the plurality of piezoelectric elements 3, as indicated by the dotted lines in FIG. 23, the respective one ends 9a may be displaced in the bending direction W relative to respective centers in the bending direction W of the piezoelectric elements 3.

Therefore, as illustrated in FIG. 22, in the present configuration, in opposite end portions in the bending direction W of the holding member 4, adjustment holes 4h1, 4h2, which are fitting portions configured to allow two arms 75, which are adjustment members configured to collectively adjust respective positions of the plurality of wirings 9, to be fitted therein, respectively, are formed.

According to such configuration as above, when the respective one ends 9a are displaced in the bending direction W relative to the respective centers in the bending direction W of the piezoelectric elements 3 as indicated by the dotted lines in FIG. 23, the two arms 75 are fitted in the respective adjustment holes 4h1, 4h2, and the two arms 75 are each moved in the bending direction W to move the holding member 4 in the bending direction W, whereby the plurality of wirings 9 held with a regular pitch in the bending direction W by the holding member 4 can collectively be moved until the respective end portions 9a are positioned at the respective centers in the bending direction W of the piezoelectric elements 3 as indicated by the solid lines in FIG. 23, enabling displacement of the respective end portions 9a to be corrected easily.

The above configuration illustrated in FIGS. 22 and 23 is applicable to the first to third embodiments described above.

An example of a configuration in which flexed portions 9k are collectively formed in a plurality of wirings 9 will be described below with reference to FIGS. 24 and 25.

Figure 24:
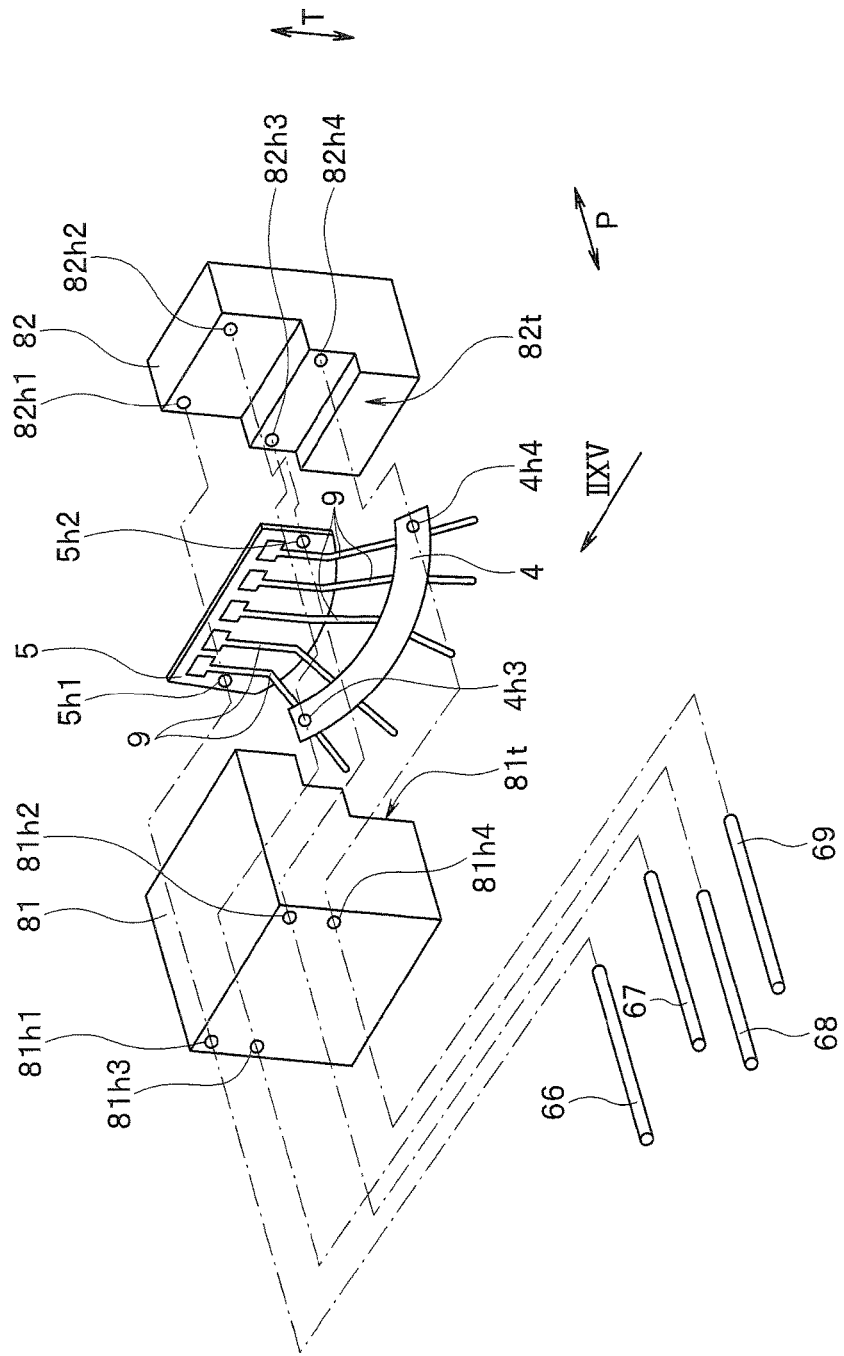
FIG. 24 is a perspective view schematically illustrating a substrate, respective wirings and a holding member in an ultrasound transducer, together with flexing dies.
Figure 25:
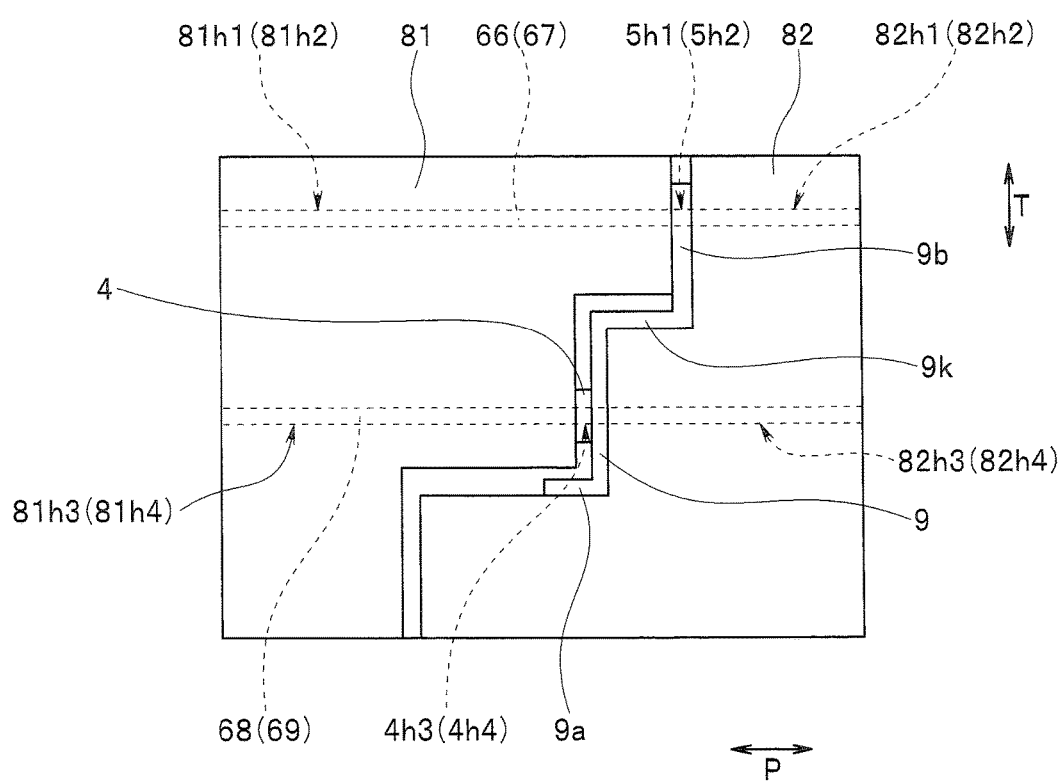
FIG. 25 is a side view of a state in which flexed portions are formed in the plurality of wirings by the flexing dies in FIG. 24, as viewed in the IIXV direction in FIG. 24.

FIG. 24 is a perspective view schematically illustrating a substrate, respective wirings and a holding member in an ultrasound transducer, together with flexing dies, and FIG. 25 is a side view of a state in which flexed portions are formed in the plurality of wirings by the flexing dies in FIG. 24, as viewed in the IIXV direction in FIG. 24.

As illustrated in FIG. 24, if flexed portions 9k such as mentioned above are formed in a plurality of wirings 9 held at a regular pitch in a bending direction W by a holding member 4, respectively, flexed portions 9k may individually be formed in the respective wirings 9; however, as illustrated in FIGS. 24 and 25, the flexed portions 9k may collectively be formed using flexing dies 81, 82.

More specifically, in a substrate 5, positioning holes 5h1, 5h2 penetrating the substrate 5 in a direction P are formed, and in the holding member 4, also, positioning holes 4h3, 4h4 penetrating the holding member 4 in the direction P are formed.

Also, the flexing dies 81, 82 have respective stair-like shapes that allow respective opposed surfaces 81t, 82t in the direction P to be fitted to each other when the flexing die 81 and the flexing die 82 are fitted together in the direction P, and furthermore, in the flexing die 81, four positioning holes 81h1, 81h2, 81h3, 81h4 penetrating the flexing die 81 in the direction P are formed, and in the flexing die 82, four positioning holes 82h1, 82h2, 82h3, 82h4 penetrating the flexing die 82 in the direction P are formed.

When the flexing dies 81 and 82 are positioned with the substrate 5, the plurality of wirings 9 and the holding member 4 therebetween in the direction P, the positioning hole 81h1 faces positioning holes 5h1, 82h1, the positioning hole 81h2 faces positioning holes 5h2, 82h2, the positioning hole 81h3 faces positioning holes 4h3, 82h3, and the positioning hole 81h4 faces positioning holes 4h4, 82h4.

Also, a positioning pin 66 is inserted through the positioning holes 81h1, 5h1, 82h1, a positioning pin 67 is inserted through positioning holes 81h2, 5h2, 82h2, a positioning pin 68 is inserted through positioning holes 81h3, 4h3, 82h3, and a positioning pin 69 is inserted through positioning holes 81h4, 4h4, 82h4.

Therefore, where a flexed portion 9k is formed in each of the plurality of wirings 9, first, the substrate 5, the plurality of wirings 9 and the holding member 4a are positioned between the stair-like opposed surface 81t of the flexing die 81 and the stair-like opposed surface 82t of the flexing die 82 in the direction P.

Subsequently, alignment is performed by inserting the positioning pin 66 through the positioning holes 81h1, 5h1, 82h1, inserting the positioning pin 67 through the positioning holes 81h2, 5h2, 82h2, inserting the positioning pin 68 through the positioning holes 81h3, 4h3, 82h3, and inserting the positioning pin 69 through the positioning holes 81h4, 4h4, 82h4.

Lastly, as illustrated in FIG. 25, the opposed surface 81t of flexing die 81 and the opposed surface 82t of the flexing die 82 are fitted to each other, whereby flexed portions 9k having a crank-like shape along the stair-like shapes of the respective opposed surfaces 81t, 82t are collectively formed in the plurality of wirings 9.

Here, since the plurality of wirings 9 are held with a regular pitch in the bending direction W by the holding member 4, the respective flexed portions 9k can collectively be formed easily in a short period of time by the respective flexing dies 81, 82 without changing the pitch of the plurality of wirings 9.

Also, the use of the flexing dies 81, 82 for forming the respective flexed portions 9k enhances accuracy in flexing angle of the flexed portions 9k and position at which the respective flexed portions 9k are formed in the respective wirings 9, enabling suppression of variation in vibration of the respective piezoelectric elements 3 of the ultrasound transducer 1.

What is claimed is:

1. An ultrasound transducer comprising:
   an acoustic matching layer bending with a predetermined curvature;
   a plurality of piezoelectric elements disposed on an inner face on a side of a curvature center of the acoustic matching layer in such a manner that the plurality of piezoelectric elements bend;
   a plurality of wirings including respective one ends electrically connected to the plurality of piezoelectric elements, respectively;
   a substrate to which respective another ends of the plurality of wirings are electrically connected; and
   a holding member provided on the plurality of wirings at a position partway of the plurality of wirings between the plurality of piezoelectric elements and the substrate, the holding member being configured to hold a pitch of the plurality of wirings so as to be a pitch that is equal to or smaller than the predetermined arrangement pitch of the plurality of piezoelectric elements.

2. The ultrasound transducer according to claim 1, wherein the holding member holds the plurality of wirings to be shifted by ½ of the pitch from the arrangement pitch of the plurality of piezoelectric elements and has a shape bending with a curvature center that is a same as the curvature center of the acoustic matching layer.

3. The ultrasound transducer according to claim 2, wherein the holding member holds the plurality of wirings in such a manner that the respective one ends of the plurality of wirings are electrically connected to respective centers in a bending direction of the plurality of piezoelectric elements.

4. The ultrasound transducer according to claim 1, wherein a position at which the respective one ends of the plurality of wirings are connected to the plurality of piezoelectric elements is located off a position at which the substrate planarly overlaps the plurality of piezoelectric elements.

5. The ultrasound transducer according to claim 1, wherein a flexed portion is formed at a position partway of each of the plurality of wirings between the respective other ends and the holding member.

6. The ultrasound transducer according to claim 1, wherein recess portions or insertion holes configured to allow the plurality of wirings to be inserted through the recess portions or insertion holes, respectively, are formed in the holding member.

7. The ultrasound transducer according to claim 1, wherein the holding member and an area of each of the plurality of wirings in which the holding member is provided are inclined at a predetermined angle relative to a direction connecting the substrate and the plurality of piezoelectric elements.

8. The ultrasound transducer according to claim 7, wherein holes or recesses portions configured to allow ultrasound radiated from the plurality of piezoelectric elements to pass through are formed in the holding member.

9. The ultrasound transducer according to claim 1, wherein a fitting portion for an adjustment member configured to collectively adjust respective positions of the plurality of wirings is formed in the holding member.

10. The ultrasound transducer according to claim 1, wherein:
    the substrate includes a first substrate, and a second substrate provided so as to be continuous with a back face of the first substrate and so as to include a potential that is a same as a potential of the first substrate, the plurality of wirings include a plurality of first wirings including respective another ends electrically connected to the first substrate, and a plurality of second wirings including respective another ends electrically connected to the second substrate, and the holding member includes a first holding member configured to hold the plurality of first wirings and a second holding member configured to hold the plurality of second wirings,
    the first holding member and the second holding member hold the plurality of first wirings and the plurality of second wirings in a staggered manner so that the plurality of first wirings and the plurality of second wirings are shifted from each other by ½ of the pitch and are directed in respective directions away from each other.

11. The ultrasound transducer according to claim 1, wherein the holding member is provided across the plurality of wirings.

12. An ultrasound endoscope including the ultrasound transducer according to claim 1.

* * * * *